United States Patent [19]

Costantini et al.

[11] 4,164,516
[45] Aug. 14, 1979

[54] PREPARATION OF 4-HYDROXY-2,4,6-TRIMETHYL-CYCLOHEXA-2,5-DIENE-1-ONE

[75] Inventors: Michel Costantini, Lyons; Michel Jouffret, Francheville Le Bas, both of France

[73] Assignee: Rhone-Poulenc Industries, Paris, France

[21] Appl. No.: 843,075

[22] Filed: Oct. 17, 1977

[30] Foreign Application Priority Data

Oct. 25, 1976 [FR] France .................. 76 33025

[51] Int. Cl.² ............................................. C07C 45/16
[52] U.S. Cl. .................................................. 260/586 P
[58] Field of Search ..................................... 260/586 P

[56] References Cited

U.S. PATENT DOCUMENTS

| | | | |
|---|---|---|---|
| 3,957,887 | 5/1976 | Ichikawa et al. | 260/586 P |
| 3,966,818 | 6/1976 | Ichikawa et al. | 260/586 P |
| 3,975,441 | 8/1976 | Ichikawa et al. | 260/586 P |
| 4,026,947 | 5/1977 | Costantini et al. | 260/586 P |

*Primary Examiner*—Norman Morgenstern
*Attorney, Agent, or Firm*—Bacon & Thomas

[57] ABSTRACT

4-Hydroxy-2,4,6-trimethyl-cyclohexa-2,5-dien-1-one ["mesitylquinol"] is prepared by oxidizing 2,4,6-trimethyl phenol ["mesitol"] with either molecular oxygen or an oxygen containing gas, in the simultaneous presence of (i) a cobalt/Schiff base complex, (ii) an amine, phosphine and/or organic phosphite co-catalyst, and, optionally, (iii) an alkali metal base.

23 Claims, No Drawings

PREPARATION OF 4-HYDROXY-2,4,6-TRIMETHYL-CYCLOHEXA-2,5-DIENE-1-ONE

BACKGROUND OF THE INVENTION

1. Field of the Invention

The present invention relates to a process for the preparation of 4-hydroxy-2,4,6-trialkyl-cyclohexa-2,5-dien-1-one, and, more especially, relates to the preparation of 4-hydroxy-2,4,6-trimethyl-cyclohexa-2,5-dien-1-one by oxidation of 2,4,6-trimethyl-phenol.

4-Hydroxy-2,4,6-trimethyl-cyclohexa-2,5-dien-1-one, more commonly known as mesitylquinol, is a compound having the structural formula:

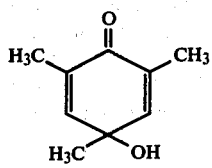

and which is a useful intermediate in the preparation of trimethylhydroquinone, the latter being an important industrial chemical employed directly as an antioxidant or as a starting material for the synthesis of vitamin E.

2. Description of the Prior Art

It is already known to the art to prepare mesitylquinol by oxidation of 2,4,6-trimethyl-phenol, hereinafter referred to simply as mesitol. Thus, E. Bamberger, Ber., 36, 2,028–41 (1903), has proposed to oxidize mesitol with Caro's acid in the presence of magnesium carbonate. This process, however, is of scant industrial value because of both the high cost of the oxidizing agent used and the resultant low yields of mesitylquinol.

The French Patent Application No. 2,177,990 also discloses a process for the preparation of mesitylquinol by oxidation of mesitol, with molecular oxygen or an oxygen containing gas. Although the conditions for carrying out this process are defined quite broadly, it has been found that the achievement of good yields of mesitylquinol is linked to the use of very high pressures of air or of oxygen, namely, of at least 100 kg/cm$^2$, and to carrying out the reaction in an aqueous solution of an alkali metal base (sodium hydroxide or potassium hydroxide). French Application No. 2,177,990 further indicates that the sodium hydroxide or potassium hydroxide can be replaced by nitrogen-containing bases such as guanidine; however, it has been found that even while utilizing an oxygen pressure of 100 kg/cm$^2$, the selectivity in respect of mesitylquinol does not exceed 29.3%. In the absence of alkali metal hydroxides, resorting to pressures of air or oxygen of at least 100 kg/cm$^2$ does not make it possible to achieve selectivities, in respect of mesitylquinol, greater than 1.1% in the absence of any catalyst or greater than 26.6% in the presence of a cobalt derivative as the catalyst. Finally, the need to resort to such high pressures of air or oxygen constitutes an obstacle to the industrial utilization of the process described in the noted French Patent Application No. 2,177,990.

SUMMARY OF THE INVENTION

The present invention specifically relates to a process for the preparation of mesitylquinol by oxidizing mesitol with oxygen or an oxygen-containing gas, which process does not require the use of high gas pressures and affords excellent yields of mesitylquinol.

More particularly, the present invention relates to a process for the preparation of 4-hydroxy-2,4,6-trimethyl-cyclohexa-2,5-dien-1-one by oxidizing 2,4,6-trimethyl phenol with molecular oxygen or an oxygen containing gas, in the liquid phase, characterized in that the reaction is conducted in the simultaneous presence of:

(i) a complex of cobalt with the Schiff bases derived from diamines and β-hydroxylic carbonyl compounds, or from enolizable β-dicarbonyl compounds, as the catalyst; and (ii) a co-catalyst selected from the group consisting of the primary, secondary and tertiary amines, the phosphines and the organic phosphites, optionally in the presence of (iii) an alkali metal base.

The process according to this invention makes it possible to obtain mesitylquinol in yields which are as high as 95% relative to the mesitol converted, under notably mild reaction conditions, for example, by conducting the reaction under an oxygen pressure equal to about atmospheric pressure and at a temperature of about 25° C.

DETAILED DESCRIPTION OF THE INVENTION

The complexes of cobalt with the Schiff bases derived from diamines and β-hydroxylic carbonyl compounds (hereinafter referred to simply as salcomines, for the sake of convenience) which are the primary catalysts in the process of the invention, are preferably those corresponding to the structural formula:

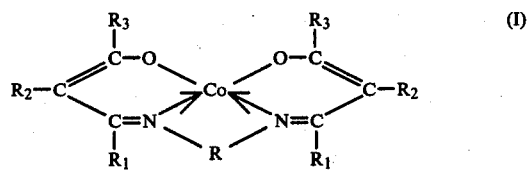

in which:
 R$_1$, R$_2$ and R$_3$, which may be the same or different, each is hydrogen or a hydrocarbon moiety, preferably a saturated hydrocarbon or an aryl moiety, having from 1 to 10 carbon atoms, and R$_2$ and R$_3$ can form, together with the two carbon atoms from which they depend, a benzene ring which is optionally substituted by 1 or 2 halogen atoms, nitro groups, hydroxyl groups, lower alkyl radicals having from 1 to 4 carbon atoms or lower alkoxy radicals having from 1 to 4 carbon atoms, and
 R is a divalent hydrocarbon radical having from 2 to 6 carbon atoms.

More preferably:
 R$_1$, R$_2$ and R$_3$ are linear or branched chain alkyl radicals such as methyl, ethyl, n-propyl, isopropyl, n-butyl, n-hexyl, n-octyl and 2-ethyl-hexyl, cycloalkyl radicals such as cyclopentyl and cyclohexyl, and aryl radicals such as phenyl and tolyl. Most preferably, R$_1$, R$_2$ and R$_3$ are lower alkyl radicals having from 1 to 4 carbon atoms and even still more preferably R$_1$ is hydrogen and R$_2$ and R$_3$ form, together with the carbon atoms from which they depend, a benzene ring which is optionally substituted by a hydroxyl group, by a lower alkyl radical or by a lower alkoxy radical having from 1 to 4 carbon atoms, and R is a linear or branched chain alkylene radical having from 2 to 6 carbon atoms in the main chain and preferably from 2 to 4 carbon atoms, such as the ethylene, methylethylene, trimethylene and tetramethylene radical, a cyclohexylene radical, or a phenylene radical such as ortho-phenylene.

The following are mentioned as exemplary of the salcomines of the formula (I): the complex of cobalt obtained from the Schiff base of acetylacetaldehyde and ethylenediamine; the complex of cobalt obtained from the Schiff base of pentane-2,4-dione and ethylenediamine; bis-(salicylal)-ethylenediimino-cobalt(II); bis-(salicylal)-trimethylenediimino-cobalt(II); bis-(salicylal)-tetramethylenediimino-cobalt(II); bis-(salicylal)-ortho-phenylenediimino-cobalt(II); bis-(3-methoxy-salicylal)-ethylenediimino-cobalt(II); bis-(3-ethoxy-salicylal)-ethylenediimino-cobalt(II); bis-(3-chloro-salicylal)-ethylenediimino-cobalt(II); bis-(3-nitro-salicylal)-ethylenediimino-cobalt(II); bis-(5-nitro-salicylal)-ethylenediimino-cobalt(II); bis-(5-methyl-salicylal)-ethylenediimino-cobalt(II); bis-(6-methyl-salicylal)-ethylenediimino-cobalt(II); bis-(4-ethoxy-salicylal)-ethylenediimino-cobalt(II); bis-(salicylal)-trimethylenediimino-cobalt(II); bis-(3-fluoro-salicylal)-trimethylenediimino-cobalt(II); bis-(3-methyl-salicylal)-trimethylenediimino-cobalt(II); bis-(5-nitro-salicylal)-trimethylenediimino-cobalt(II); bis-(5-methyl-salicylal)-trimethylenediimino-cobalt(II); bis-(3-methoxy-salicylal)-trimethylenediimino-cobalt(II); bis-(3-methoxy-salicylal)-ortho-phenylenediimino-cobalt(II); and bis-(4-hydroxy-salicylal)-ethylenediimino-cobalt-(II).

The complexes of the formula (I) are known products which can be prepared in accordance with the usual processes. For example, it is possible to employ the method described by R. H. Bailes et al in *J. Am. Chem. Soc.*, 69, page 1,886 et seq. (1947).

The amount of salcomine utilized in the subject process, represented as the number of gram-atoms of cobalt per mol of mesitol, can vary between about 0.001 and 0.2, and preferably between about 0.02 and 0.1; it is possible to operate without these limits, but such does not result in any special advantages.

The co-catalysts used in the process according to the invention can be represented by the structural formulae:

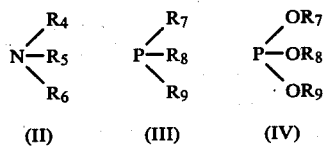

in which:

R$_4$, R$_5$ and R$_6$, which may be the same or different, are hydrocarbon radicals having from 1 to 10 carbon atoms, and at most two and preferably at most one of the radicals R$_4$, R$_5$ and R$_6$ is hydrogen and any two of which radicals can together form, especially if one of such radicals is hydrogen, an alkylene radical having from 5 to 6 carbon atoms, and R$_7$ to R$_9$, which may be the same or different, are hydrocarbon radicals having from 1 to 15 carbon atoms.

More preferably, the radicals R$_4$ to R$_9$ are alkyl radicals such as the methyl, ethyl, n-propyl, isopropyl, n-butyl, t-butyl, isobutyl, n-pentyl, hexyl, heptyl, octyl and decyl radicals; cycloalkyl radicals having from 5 to 10 carbon atoms and optionally substituted by 1 to 3 lower alkyl radicals having from 1 to 4 carbon atoms, such as the cyclopentyl, cyclohexyl, cycloheptyl, 2-methyl-cyclohexyl and 3-ethyl-cyclohexyl radicals; aryl radicals optionally substituted by 1 to 3 lower alkyl radicals having from 1 to 4 carbon atoms, such as the phenyl, biphenyl, α-naphthyl, β-naphthyl, tolyl, xylyl and 4-ethyl-phenyl radicals; and aralkyl radicals having from 1 to 4 carbon atoms in the alkyl radical, such as the benzyl, 1-phenylethyl, 2-phenyl-ethyl and 2-phenyl-propyl radicals.

As specific examples of amines of the formula (II), there are mentioned methylamine, dimethylamine, trimethylamine, diethylamine, triethylamine, n-butylamine, isobutylamine, t-butylamine, di-n-butylamine, tri-n-butylamine, di-n-pentylamine, diisopropylamine, diisobutylamine, hexylamine, 2,2-diethylhexylamine, cyclohexylamine, dicyclohexylamine, n-butylcyclohexylamine, diethyl-cyclohexylamine, aniline, diphenylamine, N-ethylaniline, N-isobutylaniline and piperidine. Preferably, the secondary and tertiary amines are utilized.

The phosphines which can be used in the process according to the invention include, without implying a limitation: triethylphosphine, tri-n-butylphosphine, triisobutylphosphine, ethyl-di-n-butylphosphine, tri-n-pentylphosphine, tri-n-hexylphosphine, tricyclohexylphosphine, di-n-butylcyclohexylphosphine, di-n-butylcyclohexylphosphine, triphenylphosphine, cyclohexyldiphenylphosphine and tritolylphosphine. As examples of the phosphites, there are mentioned trimethyl phosphite, triethyl phosphite, tri-n-butyl phosphite, tricyclohexyl phosphite, triphenyl phosphite and dimethyl phenyl phosphite.

The amount of co-catalyst, expressed as the number of mols of compounds of the formula (II) and/or (III) and/or (IV) per mol of mesitol can vary over wide limits. In fact, there is no critical upper limit because the amine and/or the phosphine and/or the phosphite can serve as a solvent for the mesitol, or as the reaction medium if they are liquid under the conditions of reaction. In general, the amount of co-catalyst is at least 0.5 mol per mol of mesitol. Preferably, at least one mol of amine and/or of phosphine and/or of phosphite is used per mol of mesitol. The amines, the phosphines and the phosphites can be used as a mixture of compounds within each category or of compounds from the different categories, in ratios which are not critical.

When the process according to the invention is carried out in the presence of an alkali metal base, such base is an alkali metal oxide or hydroxide, or an alkali metal salt of a weak inorganic or organic acid, or is an alcoholate. In general, sodium hydroxide, potassium hydroxide, lithium hydroxide, sodium carbonate, potassium carbonate, sodium methylate, potassium ethanolate or potassium t-butylate are preferred.

The amount of alkali metal base, expressed in mols per mol of mesitol, can also vary over wide limits. In general, at least 0.01, and preferably at least 0.05 mol of base is employed per mol of mesitol. Although there is no truly meaningful upper limit on the amount of base, it is generally of no value to employ more than 2 mols, and preferably no more than one mol of base per mol of mesitol.

The process feature of the present invention can be carried out in water, in an inert organic medium, or in an aqueous-organic medium; accordingly, in addition to amines, phosphines and phosphites, suitable media are organic compounds such as aliphatic hydrocarbons (e.g., hexane, heptane or octane), cycloaliphatic hydrocarbons (e.g., cyclopentane and cyclohexane), aromatic hydrocarbons (e.g., benzene, toluene and xylene) and the halogen derivatives of these various hydrocarbons; cyclic or acyclic ethers (e.g., isopropyl ether or tetrahydrofuran); esters (e.g., ethyl acetate and methyl propionate); saturated aliphatic alcohols such as methanol, ethanol, n-propanol, isopropanol, n-butanol, isobutanol, t-butanol, hexanols and octanols; amides (e.g., dimethylformamide, dimethylacetamide and N-methylpyrrolidone); and nitriles (e.g., propionitrile and acetonitrile). The saturated aliphatic alcohols containing from 1 to 10 carbon atoms are most especially suitable. It is preferred to use an organic reaction medium in which the mesitol is soluble. The concentration of the latter in this reaction medium is, however, not critical.

Though the temperature can vary over wide limits, it is not necessary, in general, to employ temperatures outside the range of from 0° to 100° C. and, in particular, it generally suffices to carry out the reaction at between 10° and 60° C.

The partial pressure of oxygen is typically near atmospheric pressure. However, it is possible to depart from this value without thereby going without the scope of the invention. Thus, it is possible to conduct the reaction at partial pressures of oxygen below atmospheric pressure, for example, pressures of at least 0.1 bar and preferably at least 0.2 bar. The use of partial pressures of oxygen greater than 1 bar does not result in any particular advantage.

As the gas containing molecular oxygen, it is contemplated to use pure oxygen or mixtures of the latter with inert gases such as nitrogen or the elements of group O of the Periodic Table (for example, argon). Typically, air depleted in oxygen or enriched in oxygen is employed in such instances.

The process according to the invention, moreover, lends itself especially well to continuous operation.

In order to further illustrate the present invention and the advantages thereof, the following specific examples are given, it being understood that the same are intended only as illustrative and in nowise limitative.

EXAMPLE 1

2.75 g of mesitol (0.0202 mol), 30 ml of isopropanol and 30 ml of di-n-butylamine were introduced into a three-necked 100 ml glass flask equipped with a stirring system revolving at 1,000 rpm, a thermometer, and an oxygen inlet tube connected to a gas storage vessel containing and supplying oxygen at atmospheric pressure.

The apparatus was then flushed with oxygen, its contents were brought to 25° C. and 0.65 g (0.002 mol) of salcomine [bis-(salicylal)-ethylenediimino-cobalt(II)] were added. The amount of oxygen absorbed, as a function of time, was then monitored on the gas storage vessel. After contact time of 5 hours, 63% of the theoretical amount of oxygen had been fixed. The stream of oxygen was then stopped and the apparatus was flushed with nitrogen. The reaction mixture was filtered and the unconverted mesitol and the mesitylquinol formed, as well as the possible by-products (for example, 2,6-dimethyl-p-benzoquinone), were then determined in the filtrate by gas-liquid chromatography. The following results were obtained:

Unconverted mesitol: 1.28 g, representing a degree of conversion of 53.2%.

Mesitylquinol: 1.66 g, representing a yield of 57.4% relative to the mesitol converted.

By way of comparison, the preceding experiment was repeated, but conducted in the absence of di-n-butylamine. After 3 hours 20 minutes, the amount of oxygen absorbed corresponds to 65.8% of the amount theoretically necessary for the conversion of the mesitol to mesitylquinol. Determination of the products by gas-liquid chromatography provided the following results:

Degree of conversion of mesitol: 85.8%,

Yield of mesitylquinol relative to mesitol converted: 15.2%,

Yield of 2,6-dimethyl-benzoquinone: 4.4%.

EXAMPLE 2

The procedure in Example 1 was repeated, with the di-n-butylamine being replaced by 5.3 g of triphenylphosphine. After a contact time of 1 hour 25 minutes, the theoretical amount of oxygen had been absorbed. The degree of conversion of the mesitol was 93.6% and the yield of mesitylquinol relative to the mesitol converted was 71%.

EXAMPLES 3 TO 18

The apparatus and the method of the preceding examples were utilized, and the reaction conditions varied; these conditions, as well as the results obtained, are shown in the table which follows:

TABLE

| Ex. | MESITOL (in g) | CATALYST (in g) | CO-CATALYST | ALKALI METAL BASE (in g) | SOLVENT (in ml) | T IN °C. | DURATION | % $O_2$ ABSORBED | DC (1) of MESITOL | YIELD (2) of MESITYLQUINOL | YIELD OF DBMQ (3) |
|---|---|---|---|---|---|---|---|---|---|---|---|
| 3 | 2.75 | Co(Salen) (4) 0.65 | di-n-butylamine 10 ml | none | isopropanol (20) | 25 | 1 hr 05 | 102 | 85.4% | 52.5% | |
| 4 | " | " | " | NaOH | " | " | 1 hr | " | 90.7% | 63.7% | |
| 5 | " | " | " | NaOH | " | " | 1 hr 40 | 100 | 90.2% | 62.7% | |
| 6 | " | Co(Salen) 0.13 | " | NaOH 0.2 | " | " | 3 hrs 45 | 115 | 86.4% | 67.1% | |
| 7 | " | " | " | " | " | 40 | 0 hr 50 | 105 | 91% | 60.6% | |
| 8 | " | Co(Salen) 0.65 | di-n-butylamine 10 ml | " | DMF (5) (20) | 25 | 2 hrs 10 | 133 | 73% | 60.3% | |
| 9 | " | " | triphenylphosphine 5.3 g | none | DMF (30) | " | 0 hr 35 | 100 | 95.3% | 80.7% | |
| 10 | " | " | di-n-butylamine 10 ml + triphenylphosphine | none | isopropanol (20) | " | 0 hr 40 | 113 | 100% | 95.1% | |

TABLE-continued

| Ex. | MESI-TOL (in g) | CATALYST (in g) | CO-CATALYST | ALKALI METAL BASE (in g) | SOLVENT (in ml) | T IN °C. | DUR-ATION | % O₂ AB-SORBED | DC (1) of MESI-TOL | YIELD (2) of MESITYL-QUINOL | YIELD OF DBMQ (3) |
|---|---|---|---|---|---|---|---|---|---|---|---|
| 11 | " | " | 5.3 g dibutylamine 30 ml | none | none | 50 | 2 hrs 30 | 110 | 77.7% | 43% | |
| 12 | " | " | triethylamine 10 ml | NaOH 0.2 | isopropanol 20 ml | 25 | 1 hr 45 | 100 | 96% | 49.6% | |
| 13 | " | Co(Salen) 0.13 | diethylamine 10 ml | NaOH 0.2 | water 9 ml | 40 | 2 hrs 25 | 100 | 89.8% | 58% | |
| 14 | " | Co(Salen) 0.65 | diphenylamine 9.8 g | " | isopropanol 20 ml | 25 | 1 hr | 103 | 97.3% | 47.4% | 5.3% |
| 15 | " | Co(4-hydroxy-Salen) (6) 0.7 | diethylamine 10 ml | none | water 20 ml | 30 | 3 hrs 30 | 100 | 98.1% | 56.1% | |
| 16 | " | Co(3-ethoxy-Salen) (7) 0.82 | di-n-butyl amine 10 ml | NaOH 0.2 | isopropanol 20 ml | 25 | 0 hr 20 | 103 | 93.8% | 58% | |
| 17 | " | Co(Salphen) (8) 0.78 | di-n-butylamine 10 ml | NaOH 0.2 | isopropanol 20 ml | 25 | 0 hr 50 | 100 | 87.9% | 57.35% | |
| 18 | " | Co(Salen) 0.65 | di-n-butylamine 10 ml + trimethyl phosphite 2.5 g | " | " | " | 0 hr 55 | 54 | 44.1% | 86.4% | |

(1) DC = degree of conversion
(2) YIELD = yield relative to mesitol converted
(3) DMBQ = 2,6-dimethyl-p-benzoquinone
(4) Co(Salen) = bis-(salicylal)-ethylenediimino-cobalt (II)
(5) DMF = dimethylformamide
(6) Co(4-hydroxy-Salen) = bis-(4-hydroxy-salicylal)ethylenediimino-cobalt(II)
(7) Co(3-ethoxy-Salen) = bis-(3-ethoxy-salicylal)ethylene-diimino-cobalt(II)
(8) Co(Salphen) = bis-(salicylal)-ortho-phenylenediimino-cobalt(II).

EXAMPLE 19

2.75 g of mesitol, 10 ml of di-n-butylamine, 20 ml of isopropanol and 0.65 g of Co(Salen) were introduced into a 250 ml stainless steel autoclave, the autoclave was then closed and air was introduced until the pressure was 100 bars. The reaction mixture was stirred for 2 hours 10 minutes at 20° C. and was then treated as in Example 1. The degree of conversion of the mesitol was 100% and the yield relative to the mesitol converted was 56.1%.

EXAMPLE 20

The procedure of Example 19 was followed, but 5.3 g of triphenylphosphine were added to the reactants previously introduced. Stirring was continued for 4 hours. The degree of conversion of the mesitol was 100% and the yield of mesitylquinol relative to mesitol converted was 99%.

While the invention has now been described in terms of certain preferred embodiments, and exemplified with respect thereto, the skilled artisan will appreciate that various modifications, changes, substitutions, and omissions may be made without departing from the spirit thereof. Accordingly, it is intended that the scope of the present invention be limited solely by that of the following claims.

What is claimed is:

1. A process for the preparation of 4-hydroxy-2,4,6-trimethyl-cyclohexa-2,5-dien-1-one, which comprises oxidizing 2,4,6-trimethyl-phenol with molecular oxygen or an oxygen containing gas, said oxidation being conducted under a partial pressure of oxygen of about 1 bar or less and in the simultaneous presence of a catalytic amount of (i) a cobalt/Schiff base complex, and (ii) a co-catalyst selected from the group consisting of an amine, a phosphine, an organic phosphite, and mixtures thereof.

2. The process as defined in claim 1, wherein the catalyst component (i) is a complex of cobalt with a Schiff base selected from the group consisting of those derived from a diamine and a β-hydroxylic carbonyl compound and those derived from an enolizable β-dicarbonyl compound.

3. The process as defined by claim 2, the catalyst further comprising (iii) an alkali metal base.

4. The process as defined by claim 2, wherein the cobalt complex has the structural formula:

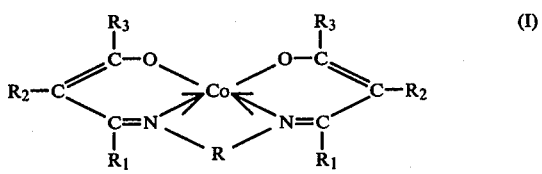

in which:
R₁, R₂ and R₃ are the same or different, and each is hydrogen or a hydrocarbon radical having from 1 to 10 carbon atoms, and R₂ and R₃ can form, together with the two carbon atoms from which they depend, a benzene ring which is optionally substituted by 1 or 2 halogen atoms, nitro groups, hydroxyl groups, alkyl radicals having from 1 to 4 carbon atoms or alkoxy radicals having from 1 to 4 carbon atoms, and
R is a divalent hydrocarbon radical having from 2 to 6 carbon atoms.

5. The process as defined by claim 4, wherein the cobalt complex R is a member selected from the group consisting of an alkylene radical having from 2 to 4 carbon atoms and an ortho-phenylene radical.

6. The process as defined by claim 4, wherein the cobalt complex is selected from the group consisting of bis(salicylal)-ethylene-diimino-cobalt(II), bis-(4-hydroxy-salicylal)-ethylenediimino-cobalt(II), bis-(3-ethoxy-salicylal)-ethylenediimino-cobalt(II), bis-(salicylal)-trimethylenediimino-cobalt(II), and bis-(salicylal)-ortho-phenylenediimino-cobalt(II).

7. The process as defined by claim 4, wherein the co-catalyst (ii) is an amine having the structural formula:

 (II)

in which:
R$_4$, R$_5$ and R$_6$ are the same or different, and each is hydrogen or a hydrocarbon radical having from 1 to 10 carbon atoms, at most two of the radicals R$_4$, R$_5$ and R$_6$ being hydrogen, and, if but a single such radical is hydrogen, the remaining two together may form an alkylene radical having from 5 to 6 carbon atoms.

8. The process as defined by claim 7, wherein the amine of the formula (II), each R$_4$, R$_5$ and R$_6$ is selected from the group consisting of alkyl, cycloalkyl, aryl and aralkyl.

9. The process as defined by claim 7, wherein the amine of the formula (II) is selected from the group consisting of diethylamine, triethylamine, diisobutylamine, di-n-butylamine and diphenylamine.

10. The process as defined by claim 4, wherein the co-catalyst (ii) is a phosphine having the structural formula:

 (III)

in which:
R$_7$, R$_8$ and R$_9$ are the same or different, and each is a hydrocarbon radical having from 1 to 15 carbon atoms.

11. The process as defined by claim 8, wherein the phosphines of the formula (III), each R$_7$, R$_8$ and R$_9$ is selected from the group consisting of alkyl, cycloalkyl, aryl and aralkyl.

12. The process as defined by claim 9, wherein the phosphine is triphenylphosphine.

13. The process as defined by claim 4, wherein the co-catalyst (ii) is an organic phosphite having the structural formula:

 (IV)

in which:
R$_7$, R$_8$ and R$_9$ are the same or different, and each is a hydrocarbon radical having from 1 to 15 carbon atoms.

14. The process as defined by claim 13, wherein the phosphite is trimethyl phosphite.

15. The process as defined by claim 4, wherein the co-catalyst (ii) is a mixture of phosphines, amines and/or phosphites.

16. The process as defined by claim 4, the catalyst further comprising (iii) an alkali metal base selected from the group consisting of an oxide, hydroxide, alcoholate, and salt of an alkali metal with a weak inorganic or organic acid.

17. The process as defined by claim 16, wherein the alkali metal base is selected from the group consisting of sodium hydroxide and potassium hydroxide.

18. The process as defined by claim 4, wherein the amount of cobalt complex represented by the number of gram-atoms of cobalt per mol of 2,4,6-trimethyl-phenol is between 0.001 and 0.2.

19. The process as defined by claim 4, wherein the amount of co-catalyst expressed in mols of amine and/or of phosphine and/or of phosphite per mol of 2,4,6-trimethyl-phenol is at least 0.5.

20. The process as defined by claim 3, wherein the amount of alkali metal base is at least 0.01 mol per mol of 2,4,6-trimethyl-phenol.

21. The process as defined by claim 2, wherein the oxidation is carried out at a temperature of between 0° to 100° C., and under a partial pressure of oxygen of at least 0.1 bar.

22. The process as defined by claim 2, wherein the oxidation is carried out in a member selected from the group consisting of water and an inert organic diluent.

23. The process as defined by claim 22, wherein an excess of amine, phosphine or phosphite, or an amide, an alcohol, a nitrile, an ether, an ester or a halogenated or non-halogenated hydrocarbon is employed as the reaction medium.

* * * * *